US005672873A

United States Patent [19]
Yamazoe

[11] Patent Number: 5,672,873
[45] Date of Patent: Sep. 30, 1997

[54] METHOD AND APPARATUS FOR QUANTITATIVE DETERMINATION OF COMPONENTS IN RESIDUAL FUEL OILS

[75] Inventor: Seigo Yamazoe, Saitama, Japan

[73] Assignees: Cosmo Research Institute; Cosmo Oil Co., Ltd., both of Tokyo, Japan

[21] Appl. No.: 679,502

[22] Filed: Jul. 12, 1996

[30] Foreign Application Priority Data

Jul. 13, 1995 [JP] Japan ................................. 7-199258

[51] Int. Cl.$^6$ ............................ G01N 21/25; G01N 21/27
[52] U.S. Cl. ................... 250/339.12; 250/343; 250/573; 356/70; 356/442
[58] Field of Search ............................. 250/339.12, 343, 250/573, 576; 356/70, 436, 442

[56] References Cited

U.S. PATENT DOCUMENTS

| 4,843,247 | 6/1989 | Yamazoe et al. | |
|---|---|---|---|
| 4,940,900 | 7/1990 | Lambert | 250/343 |

FOREIGN PATENT DOCUMENTS

| 0 304 233 | 2/1989 | European Pat. Off. | |
|---|---|---|---|
| 0 346 609 | 12/1989 | European Pat. Off. | |
| 2-248844 | 10/1990 | Japan | 356/70 |

OTHER PUBLICATIONS

"Rapid method of Determination of Asphaltene Content in Petroleum Crudes and Products", Mirsayapova et al., Chemistry and Technology of Fuels and Oils, vol. 12, No. 9/10, Jan. 1, 1976, pp. 805–807.

"Mesure de la Teneur en Asphaltenes des Coupes Lourdes du Petrole par Spectrophotometrie", Bouquet et al., International Symposium on Characterization of Heavy Crude Oils and Petroleum Residues, Jun. 25, 1984, pp. 196–199.

Revue de L'Institut Francais du Petrole, vol. 38 No. 1, Jan. 1983, Paris Fr., pp. 101–120, XP002016861, G. Hotier et al., the whole document.

Primary Examiner—Edward J. Glick
Attorney, Agent, or Firm—Sughrue, Mion, Zinn, Macpeak & Seas

[57] ABSTRACT

In a method and an apparatus for determining a content of an aliphatic hydrocarbon insoluble matter in a residual fuel oil, the method includes the steps of: (a) measuring absorbances of a sample solution having an aliphatic hydrocarbon insoluble matter suspended in the sample solution at two spaced wavelengths of light in a wavelength range from 500 nm to 1,000 nm; and (b) performing an operation to determine the content of the aliphatic hydrocarbon insoluble matter in the sample solution by inserting the measured absorbances into the specific correlations. The contents of the insoluble matter in aliphatic hydrocarbons and asphaltene in the residual fuel oil can be determined in a precise and rapid manner even if the oil contains the particles of aromatic hydrocarbons such as toluene.

20 Claims, 2 Drawing Sheets

METHOD AND APPARATUS FOR QUANTITATIVE DETERMINATION OF COMPONENTS IN RESIDUAL FUEL OILS

BACKGROUND OF THE INVENTION

1. Field of the Invention

The present invention relates to a method and apparatus for achieving rapid determination of the content of an aliphatic hydrocarbon insoluble matter and asphaltene in residual fuel oils such as atmospheric residue, vacuum residue, hydrocracked oil, thermally cracked oil, shale oil and tar sand oil.

2. The Related Art

Residual fuel oils are commonly evaluated by a solvent insolubility test which is carried out using n-heptane as the solvent. This is one of the important tests for evaluating residual fuel oils since it is used to evaluate the quality of fuel oils while providing a measure of the efficiency of cracking in an apparatus for cracking residual fuel oils.

It is an established practice to determine the content of an n-heptane insoluble matter according to the method specified by the Institute of Petroleum (UK) (IP143, which is hereunder abbreviated as the "IP method"). According to the IP method, a sample is dissolved in a prescribed amount of n-heptane and the solution is filtered to collect the insoluble matter on the filter paper, which is washed with a Soxhlet's extractor under reflex with n-heptane and subjected to extraction with toluene An a Soxhlet's extractor, with the extracted soluble content being determined as the content of asphaltene. This procedure has the disadvantage that it involves complicated operations and requires as many as 9 hours to complete the analysis.

There is another method for determining the content of an n-heptane insoluble matter. This is the method of Universal Oil Product Co. (UOP614/80, which is hereinafter referred to as the "UOP method") and adopted at certain plants. According to the UOP method, a sample is dissolved or suspended in a prescribed amount of n-heptane and the solution or suspension is passed through a membrane falter and the amount of the insoluble matter collected on the filter is determined gravimetrically as the content of asphaltene.

However, the UOP method is also a time-consuming process (requires about 4 hours to complete the analysis) and, in addition, the result does not agree with the data obtained by the IP method.

Under the circumstances, the present inventor previously proposed a dual wavelength spectrophotometric method (hereunder referred to simply as the 2A method) that could determine the content of an n-heptane insoluble matter or asphaltene without suffering from the conventional drawbacks (see U.S. Pat. No. 4,843,247).

The 2A method is superior to the conventional techniques since it involves very simple operations, requires a shorter processing time and achieves a higher precision in quantitative determination.

However, when the 2A method was applied to various kinds of residual fuel oils for determining the content of the n-heptane insolubles, the results of determination on the oil species containing toluene-insoluble particles turned out to be different from the data obtained by the UOP method.

Furthermore, when the 2A method was applied to determine the content of asphaltene in various kinds of residual fuel oils, the results of determination on the oil species containing toluene-insoluble particles turned out to be different from the data obtained by the IP method.

SUMMARY OF THE INVENTION

The present invention has been accomplished under these circumstances and has as an object providing a method by which the contents of an aliphatic hydrocarbon insoluble matter and asphaltene in residual fuel oils can be determined in a precise and rapid manner even if the oils contain toluene-insoluble particles and which is equally applicable to oil species that do not contain any toluene-insoluble particles. Another object of the invention is to provide an apparatus for implementing the method.

The present inventor conducted intensive studies with a view to solving the conventional problems. As a result, when a sample solution prepared by adding an aromatic hydrocarbon to a residual fuel oil containing toluene-insoluble particles in such a way that the oil and the hydrocarbon would dissolve in each other, followed by the addition of an aliphatic hydrocarbon to coagulate an aliphatic hydrocarbon insoluble matter was illuminated with light at two wavelengths, the rate of increase in the absorbance of the sample solution or the ratio of its absorbances could be correlated with the relative proportion of the aliphatic hydrocarbon insoluble matter by a certain formula. The inventor also found that when this formula was combined with another formula that correlated the content of the aliphatic hydrocarbon insoluble matter to both the absorbance of the sample solution at either one wavelength and the absorbance of the sample solution which eliminated the aliphatic hydrocarbon insoluble matter at the one wavelength and when the measured values of the absorbances were inserted into the combination correlation followed by performance of the necessary mathematical operations, the content of the hydrocarbon insoluble matter in the residual fuel oil containing the toluene-insoluble particles could be determined in an as precise and rapid manner as with residual fuel oils that did not contain any toluene-insoluble particles. The present invention has been accomplished on the basis of these findings.

The same inventive concept applies to the asphaltene content of residual fuel oils. The inventor found that the rate of increase in the absorbance of a sample solution illuminated with light at two wavelengths or the ratio of absorbance with light at two wavelengths could correlate with the asphaltene fraction relative to the aliphatic hydrocarbon insoluble matter by a certain formula where the asphaltene fraction is a value of the asphaltene content divided by the aliphatic hydrocarbon insoluble matter. The inventor also found that when the formula was combined with the second correlation described in the previous paragraph and when the measured values of the absorbances were inserted into the combination correlation followed by performance of the necessary calculations, the content of asphaltene in the residual fuel oil containing the toluene-insoluble particles could be determined in an as precise and rapid manner as with residual fuel oils that did not contain any toluene-insoluble particles. The present invention has also been accomplished on the basis of these findings.

Thus, according to its first aspect, the present invention provides a method of determining the content of an aliphatic hydrocarbon insoluble matter in a residual fuel oil, which includes; adding an aromatic hydrocarbon to a sample of the residual fuel oil such that they dissolve in each other; then adding an aliphatic hydrocarbon to the resulting mixture to coagulate the aliphatic hydrocarbon insoluble matter, thereby preparing a sample solution having the aliphatic hydrocarbon insoluble matter suspended in the solvent; measuring the absorbances $K_3$ and $K_4$ of the sample solution at two spaced wavelengths of light in the wavelength range from 500 nm to 1,000 nm; inserting the measured values of $K_3$ and $K_4$ into one of the following correlations:

the content of the aliphatic hydrocarbon insoluble matter=$\{a(bK_3-cK_4)\} \times 100/\{d((K_4-K_3) \times 100/K_3)+e\}$ where a is 0.015 to 0.035; b is 1 to 10; c is 0.5 to 7; d is −10 to −0.1; e is 50 to 300; or the content of the aliphatic hydrocarbon insoluble matter=$\{a(bK_3-cK_4)\}\times 100/\{d(K_4\times 100/K_3)+e\}$ where a is 0.015 to 0.035; b is 1 to 10; c is 0.5 to 7; d is −800 to −500; e is 500 to 1,000; and performing the necessary mathematical operations to determine the content of the aliphatic hydrocarbon insoluble matter in the sample solution.

The invention also provides a method of determining the content of asphaltene in a residual fuel oil, which includes: adding an aromatic hydrocarbon to a sample of the residual fuel oil such that they dissolve in each other; then adding an aliphatic hydrocarbon to the resulting mixture to coagulate the aliphatic insoluble matter, thereby preparing a sample solution having the aliphatic hydrocarbon insoluble matter suspended in the solvent; measuring the absorbances $K_3$ and $K_4$ at two spaced wavelengths of light in the wavelength range from 500 nm to 1,000 nm; inserting the measured values of $K_3$ and $K_4$ into one of the following correlations:

the content of asphaltene=$\{a(bK_3-cK_4)\}\times 100/\{d((K_4-K_3)\times 100K_3)+e\}\times\{f((K_4-K_3)\times 100/K_3)+g\}/100$ where a is 0.015 to 0.035; b is 1 to 10; c is 0.5 to 7; d is −10 to −0.1; e is 50 to 300; f 1 to 30; g is −5 to 5; or the content of asphaltene=$\{a(bK_3-cK_4)\}\times 100/\{d(K_4\times 100/K_3)+e\}\times\{f(K_4\times 100/K_3)+g\}/100$ where a is 0.015 to 0.035; b is 1 to 10; c is 0.5 to 7; d is −800 to −500; e is 500 to 1,000; f is 450 to 550; g is −600 to −300; and performing the necessary mathematical operations to determine the content of asphaltene in the sample solution.

According to its second aspect, the present invention provides an apparatus for determining the content of an aliphatic hydrocarbon insoluble matter in a residual fuel oil, which includes: a container of a sample solution which has been prepared by adding an aromatic hydrocarbon to a sample of the residual fuel oil such that they dissolve in each other, then adding an aliphatic hydrocarbon to the resulting mixture to coagulate the aliphatic hydrocarbon insoluble matter such that it is suspended in the solvent; a dip probe or a flow cell for taking a predetermined portion of the sample solution which are provided in a face-to-face relationship with the inner surface of a sidewall of the container and which are capable of approaching or departing from the latter; a two-wavelength detector including a light source, passages for the light from the source to be transmitted through a given thickness of the sample solution within the dip probe or flow cell, two interference filters that permit selective passage of the transmitted light at two different wavelengths in a range of 500 to 1,000 nm, and phototubes or photocells which convert the intensities of the incident light and the transmitted light to values of an electric current; and a calculator which converts the thus obtained current values to the content of the aliphatic hydrocarbon insoluble matter by insertion into one of the following correlations:

the content of the aliphatic hydrocarbon insoluble matter=$\{a(bK_3-cK_4)\}\times 100/\{d((K_4-K_3)\times 100/K_3)+e\}$ where a is 0.015 to 0.035; b is 1 to 10; c is 0.5 to 7; d is −10 to −0.1; e is 50 to 300; and $K_3$ and $K_4$ are the absorbances at the two selected wavelengths; or the content of the aliphatic hydrocarbon insoluble matter=$\{a(bK_3-cK_4)\}\times 100/\{d(K_4\times 100/K_3)+e\}$ where a is 0.015 to 0.035; b is 1 to 10; c is 0.5 to 7; d is −800 to −500; e is 500 to 1,000; and $K_3$ and $K_4$ are the absorbances at the two selected wavelengths.

The invention also provides an apparatus for determining the content of asphaltene in a residual fuel oil, which includes: a container of a sample solution which has been prepared by adding an aromatic hydrocarbon to a sample of the residual fuel oil such that they dissolve in each other, then adding an aliphatic hydrocarbon to the resulting mixture to coagulate the aliphatic hydrocarbon insoluble matter such that it is suspended in the solvent; a dip probe or a flow cell for taking a predetermined portion of the sample solution which are provided in a face-to-face relationship with the inner surface of a sidewall of the container and which are capable of approaching or departing from the latter; a two-wavelength detector including a light source, passages for the light from the source to be transmitted through a given thickness of the sample solution within the dip probe or flow cell, two interference filters that permit selective passage of the transmitted light at two different wavelengths in a range of 500 to 1,000 nm, and phototubes or photocells which convert the intensities of the incident light and the transmitted light to values of an electric current; and a calculator which converts the thus obtained current values to the content of the aliphatic hydrocarbon insoluble matter by insertion into one of the following correlations:

the content of asphaltene=$\{a(bK_3-cK_4)\}\times 100/\{d((K_4-K)\times 100/K_3)+e\}\times\{f((K_4-K_3)\times 100/K_3)+g\}/100$ where a is 0.015 to 0.035; b is 1 to 10; c is 0.5 to 7; d is −10 to −0.1; e is 50 to 300; f is 1 to 30; g is −5 to 5; and $K_3$ and $K_4$ are the absorbances at the two selected wavelengths; or the content of asphaltene=$\{a(bK_3-cK_4)\}\times 100/\{d(K_4\times 100/K_3)+e\}\times\{f(K_4\times 100/K_3)+g\}/100$ (16)

where a is 0.015 to 0.035; b is 1 to 10; c is 0.5 to 7; d is −800 to −500; e is 500 to 1,000; f is 450 to 550; g is −600 to −300; and $K_3$ and $K_4$ are the absorbances at the two selected wavelengths.

DESCRIPTION OF THE PREFERRED EMBODIMENTS

The present invention will now be described in detail.

The sample solution to be used in the invention is prepared by the following procedure: an aromatic hydrocarbon is added to a sample of the residual fuel oil to be analyzed such that they dissolve in each other; thereafter, an aliphatic hydrocarbon is added to the mixture to coagulate asphaltene, so that the aliphatic hydrocarbon insoluble matter (i.e., the asphaltene or the aromatic hydrocarbon insoluble matter) is suspended in the solvent.

Residual fuel oils to be analyzed are generally of the following three types: (1) those which do not contain dry sludge but which contain an insoluble matter that coagulates upon addition of aliphatic hydrocarbons such as n-heptane, the insoluble matter being capable of dissolving in toluene and other aromatic hydrocarbons; (2) those which contain dry sludge that is insoluble in aliphatic hydrocarbons such as n-heptane and which also contain an insoluble matter that coagulates upon addition of aliphatic hydrocarbons such as n-heptane, the insoluble matter being capable of dissolving in aromatic hydrocarbons such as toluene; and (3) those which contain an insoluble matter that coagulates upon addition of n-heptane and other aliphatic hydrocarbons and which also contain dry sludge that is insoluble in aliphatic hydrocarbons such as n-heptane, the insoluble matter being insoluble in aromatic hydrocarbons such as toluene.

Among these residual fuel oils, the third one is the best suited for the practice of the method of the invention since utmost precision and rapidity is assured in determinations. However, the method of the invention is also applicable to the analysis of residual fuel oils (1) and (2).

While the content of the matter that is insoluble in aromatic hydrocarbons such as toluene is not limited to any particular values, the matter is preferably contained in the residual fuel oil in an amount no more than 50 wt% of the aliphatic hydrocarbon insoluble matter.

The process of preparing the sample solution starts with adding an aromatic hydrocarbon to a sample of the residual fuel oil to be analyzed such that they dissolve in each other or that the added aromatic hydrocarbon is suspended in the oil. While various aromatic hydrocarbons may be added as exemplified by toluene, xylene and benzene, toluene is preferred. The amount of addition of aromatic hydrocarbons is not limited to any particular values and they are typically added in amounts of 30 to 1,000 parts by weight, preferably 50 to 500 parts by weight, per 100 parts by weight of the residual fuel oil. In the next step, an aliphatic hydrocarbon is added to the mixture having the aromatic hydrocarbon and the residual fuel oil dissolved In each other. While various aliphatic hydrocarbons such as those having 5 to 12 carbon atoms as exemplified by n-pentane, n-heptane, n-hexane end n-octane may be added, n-heptane is preferred. The aliphatic hydrocarbons are preferably added under heating. An appropriate temperature range for the aliphatic hydrocarbons to be added is typically from about 40° C. to about 90° C. and a temperature of about 80° C. is preferred. The amount of addition of aliphatic hydrocarbons is not limited to any particular values and they are typically added in amounts of 500 to 2,000 parts by weight, preferably 1,000 to 1,500 parts by weight, per 100 parts by weight of the residual fuel oil. The addition of the aliphatic hydrocarbon causes the coagulation of the asphaltene which has been dissolved into the residual fuel oil as the result of addition of the aromatic hydrocarbon. The particles of the coagulating asphaltene are uniform in size and range from 1 μm to 3 μm.

The sample solution is preferably cooled or left to cool before absorbance Is measured et two wavelengths. When cooled or left to cool, the temperature of the sample solution is preferably at room temperature and, in a particularly preferred embodiment, the temperature is between 25° C. and 30° C.

The present invention is an improvement of the dual wavelength spectrophotometric method. In a preferred embodiment of this method, an aromatic hydrocarbon is added to a residual fuel oil sample such that they dissolve in each other; thereafter, an aliphatic hydrocarbon is added to the resulting mixture, causing asphaltene or an aliphatic hydrocarbon insoluble matter to coagulate; the mixture is then cooled or left to cool to prepare a sample solution having the asphaltene or the aliphatic hydrocarbon insoluble matter suspended in the solvent. Subsequently, the sample solution is illuminated with light at two spaced wavelengths in the wavelength range from 500 nm to 1,000 nm and absorbance is measured at the two wavelengths. The thus measured values of absorbance are inserted into a formula that correlates the content of the asphaltene or aliphatic hydrocarbon insoluble matter to both the absorbance of the sample solution at either one wavelength and the absorbance of the sample solution which eliminates the aliphatic hydrocarbon insoluble matter at the one wavelength and the necessary mathematical operations are performed to determine the content of the asphaltene or aliphatic hydrocarbon insoluble matter in the sample solution.

The two wavelengths of light in the wavelength range from 500 nm to 1,000 nm are preferably spaced apart by at least about 10 nm and more preferably spaced apart by 30 to 150 nm.

The operating principle of the dual wavelength spectrophotometric method is such that with samples of residual fuel oils that contain both asphaltene and a maltene which is a matter soluble in aliphatic hydrocarbons (e.g. n-heptane) but which does not contain a matter that is insoluble in aromatic hydrocarbons (e.g. toluene), the absorbance at two appropriately spaced wavelengths of light in the wavelength range of 500 nm to 1,000 nm does not peak but has a tendency to decrease almost linearly toward the longer wavelength.

If the absorbances at two wavelengths of the sample solution containing a maltene and asphaltene are written as $K_3$ and $K_4$, their values differ with wavelength. If the asphaltene is removed from the sample solution, a maltene solution is left; if the absorbances of this maltene solution at the two wavelengths are written as $K_1$ and $K_2$, their values also differ with wavelength. If the absorbances of a suspension of asphaltene particles at the two wavelengths are written as $K_5$ and $K_6$, their values are also dependent on wavelength.

Figure 1:
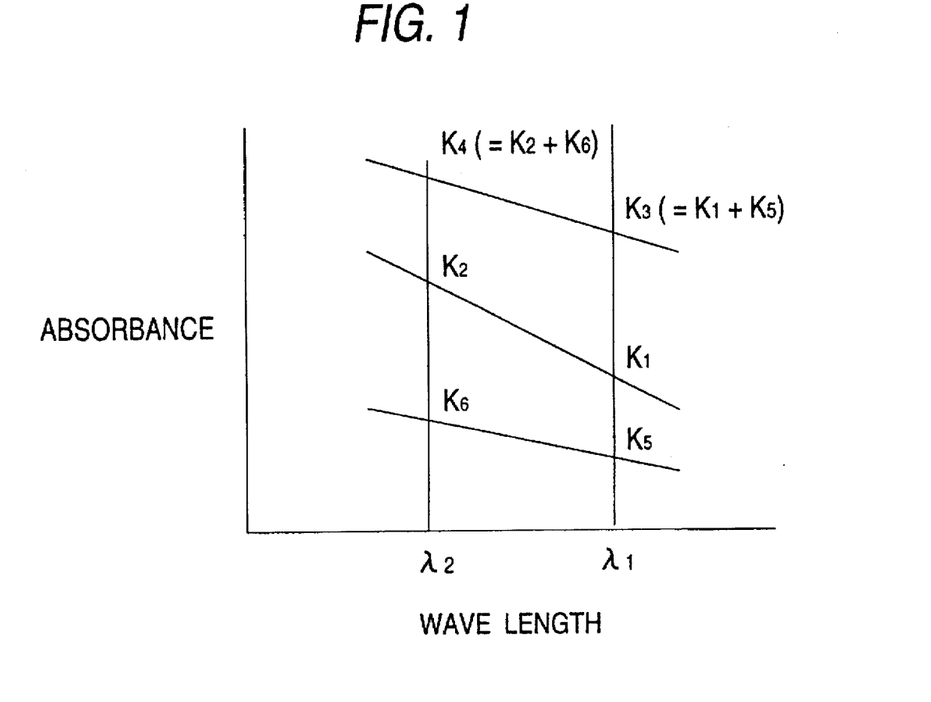
FIG. 1 is an example of a spectrum diagram illustrating the absorbances of transmitted light through a sample solution under varying conditions within the wavelength range of wavelengths.

The relationships between the respective values of absorbance are illustrated in FIG. 1.

The sample of a residual fuel oil which contains both a maltene and asphaltene but which does not contain a matter that is insoluble in toluene and other aromatic hydrocarbons is of such a character that rate of increase in the absorbance of the sample solution maintains a linear correlationship with $K_1 \times 100 / K_3$ (hereunder designated a blank rate) even if the species of the residual fuel oil or its asphaltene content varies.

Therefore, if the absorbance of the sample solution is measured at two wavelengths as the asphaltene particles remain suspended, $K_1$ of the absorbance of maltene for light having a wavelength of analysis can be obtained from the correlation between the rate of increase in the absorbance of the sample solution and the blank rate. By subtracting $K_1$ from $K_3$ which is the absorbance of the sample solution having the asphaltene particles suspended therein, one can determine $K_5$, or the absorbance of the asphaltene per se.

If a calibration curve is preliminarily constructed using a standard asphaltene which is desirably prepared in accordance with the IP method one can determine the content of asphaltene in the sample solution corresponding to $K_5$ on the basis of the calibration curve; the determined asphaltene content is then divided by the weight of the residual fuel sample to calculate the content of the asphaltene in the oil.

The rate of increase in the absorbance of the sample solution containing both maltene and asphaltene is expressed by:

$$(K_4-K_3)\times 100/K_3 \qquad (1)$$

Another way to determine the content of asphaltene in the sample oil is by using a calibration curve on the basis of the absorbance $K_3$ and $K_4$. This approach uses the linear correlationship that holds between the ratio of $K_4/K_3$ and the absorbance fraction of maltene which is expressed by $K_1/(K_1+K_3)$. By inserting the measured values of $K_3$ and $K_4$ at two wavelengths into a predetermined formula representing that correlationship, one can determine the absorbance fraction of the maltene and then calculate the absorbance of asphaltene $K_5$ by the equation $K_5 \times K_1 \times (1-$the absorbance fraction of maltene$)$.

If a calibration curve is preliminarily constructed using a standard asphaltene which is desirably prepared in accordance with the IP method, one can determine the content of asphaltene in the sample solution corresponding to $K_5$ on the basis of the calibration curve; the determined asphaltene content is then divided by the weight of the residual fuel oil sample to calculate the content of the asphaltene in the oil.

The correlationship used in this alternative approach is expressed by:

$$\text{Content of asphaltene (wt\%)}=a(bK_3-cK_4)\times 100 /G \qquad (2)$$

where a is 0.015 to 0.035, preferably 0.02 to 0.03; b is 1 to 10, preferably 1 to 7; c is 0.5 to 7, preferably 0.7 to 5; and G is the weight of the residual fuel oil sample.

This formula (2) shows that the content of asphaltene in the sample oil is equal to $a(bK_3-cK_4)$.

It should be noted here that with samples of residual fuel oils that contain both a maltene and asphaltene but which does not contain a matter insoluble in aromatic hydrocarbons such as toluene, the content of asphaltene coincides with the content of the matter insoluble in aliphatic hydrocarbons such as n-heptane. Therefore, the content of asphaltene that is determined by either of the techniques described above may substitute for the content of the matter insoluble in aliphatic hydrocarbons such as n-heptane.

If, on the other hand, the residual fuel oil sample to be analyzed contains a matter insoluble in aromatic hydrocarbons such as toluene, the value of 2A.HI which represents the content of the matter insoluble in aliphatic hydrocarbons such as n-heptane and which is measured by the 2A method comes out different from the UOP.HI value as measured by the UOP method. In other words, the value of 2A.HI for the content of the matter insoluble in an aliphatic hydrocarbon (e.g. n-heptane) deviates from the UOP.HI value and cannot be accepted as the correct value of measurement.

To deal with this problem, the value of 2A.HI is corrected in the present invention.

It should also be noted that if the residual fuel oil sample to be analyzed contains a matter insoluble in aromatic hydrocarbons such as toluene, the value of 2A.AS which represents the content of asphaltene as measured by the 2A method also comes out different from the IP.AS value as measured by the IP method.

To deal with this problem, the 2A.AS value is also corrected in the present invention.

The correction of 2A.HI is based on the fact that the fraction of the 2A.HI value divided by the UOP.HI value (which is hereunder referred to as the "relative proportion of e matter insoluble in aliphatic hydrocarbons") is correlated to the rate of increase in the absorbance of the sample solution by the following equation:

$$\text{Relative proportion of the aliphatic hydrocarbon insoluble matter}=d(\text{the rate of increase in the absorbance of the sample solution})+e \qquad (3)$$

where d is $-10$ to $-0.1$, preferably $-0.3$ to $-6$, and e is 50 to 300, preferably 70 to 250.

The thus determined relative proportion of the insoluble matter in aliphatic hydrocarbons maybe inserted into the following equation to calculate the weight of that insoluble matter:

$$\text{Content of aliphatic hydrocarbon insoluble matter}=2A.HI\times 100 /\text{relative proportion of the matter} \qquad (4)$$

Eqs. 3 and 4 may be combined as follows:

$$\text{Content of aliphatic hydrocarbon insoluble matter}=\{a(bK_3-cK_4)\}\times 100/\{d(K_4-K_3)\times 100/K_3)+e\} \qquad (5)$$

Thus, the content of the aliphatic hydrocarbon insoluble matter can be determined on the basis of the measured absorbances $K_3$ and $K_4$ of the sample solution at two wavelengths and this content may be divided by the weight of the residual fuel oil sample to calculate the content of the aliphatic hydrocarbon insoluble matter.

Eq. 5 may be applied as it is; alternatively, it may be divided into Eqs. 2 to 5 which are applied stepwise; if desired, it may be rearranged into another equation which is easier to apply.

The relative proportion of the aliphatic hydrocarbon insoluble matter can also be determined using the ratio of two absorbances of the sample solution as follows:

$$\text{Relative proportion of aliphatic hydrocarbon insoluble matter}=d\times(\text{absorbance ratio of sample solution})+e \qquad (6)$$

where d is $-800$ to $-500$, preferably $-700$ to $-600$, and e is 500 to 1,000, preferably 700 to 900.

In the next step, the thus determined relative proportion of the aliphatic hydrocarbon insoluble matter is inserted into the following equation to calculate the weight of the insoluble matter as in the method using the rate of increase in the absorbance of the sample solution:

$$\text{Content of aliphatic hydrocarbon insoluble matter}=\{a(bK_3-cK_4)\}\times 100/d\{K_4\times 100/K_3)+e\} \qquad (7)$$

Thus, the content of the aliphatic hydrocarbon insoluble matter can be determined on the basis of the absorbance ratio $K_4/K_3$ as effectively as in the case of using the rate of increase in the absorbance of the sample solution. It should be noted here that as in the already discussed case, Eq. 7 may either be applied as such or divided into a plurality of equations that are applied stepwise.

If the residual fuel oil sample contains the insoluble matter in aliphatic hydrocarbons such as toluene, the value of 2A.AS is also corrected. To this end, the fraction of the IP.AS value divided by the UOP.HI value (which is hereunder referred to as the IP.AS fraction) is correlated to the rate of increase in the absorbance of the sample solution by the following equation:

$$\text{IP.AS fraction}=f\times(\text{the rate of increase in the absorbance of sample solution})+g \qquad (8)$$

where f is 1 to 30, preferably 3 to 20, and g is $-5$ to 5, preferably $-3$ to 3.

The content of the aliphatic hydrocarbon insoluble matter as calculated by Eq. 4 or 5 and the IP.AS fraction as calculated by Eq. 8 are inserted into the following equation to determine the weight of the asphaltene contents:

$$\text{Asphaltene content}=\text{content of aliphatic hydrocarbon insoluble matter}=\text{IP.AS fraction}/100 \qquad (9)$$

Hence, Eqs. 8 and 9 may be combined as follows:

$$\text{Asphaltene content} = \{a(bK_3 - cK_4)\} \times 100/\{d(K_4 - K_3) \times 100/K_3) + e\} \times \{f((K_4 - K_3) \times 100/K_3) + g\}/100 \quad (10)$$

Thus, the asphaltene content can be determined on the basis of the measured absorbances $K_3$ and $K_4$ of the sample solution at two wavelengths and this content may be divided by the weight of the residual fuel oil sample to calculate the content of asphaltene.

Eq. 10 may be applied as it is; alternatively, it may be divided into Eqs. 2 to 9 which are applied stepwise; if desired, it may be rearranged into another equation which is easier to apply.

The asphaltene content can also be determined using the ratio of two absorbances of the sample solution as follows:

$$\text{IP.AS fraction} = f \times (\text{absorbance ratio of sample solution}) + g \quad (11)$$

where f is 450 to 550, preferably 480 to 530, and g is −600 to −300, preferably −500 to −400.

In the next step, the thus determined IP.AS fraction is inserted into the following equation to calculate the asphaltene content as in the method using the rate of increase in the absorbance of the sample solution:

$$\text{Asphaltene content} = \{a(bK_3 - cK_4)\} \times 100/\{d(K_4 \times 100/K_3) + e\} \times \{f(K_4 \times 100/K_3) + g\}/100 \quad (12)$$

Thus, the asphaltene content can be determined on the basis of the absorbance ratio as effectively as in the case of using the rate of increase in the absorbance of the sample solution. It should be noted here that as in the already described case, Eq. 12 may either be applied as such or divided into a plurality of equations that are applied stepwise.

The apparatus of the invention has a calculator which, on the basis of the values of electric current as obtained by conversion from the intensities of both incident and transmitted light, inserts the respective values into the associated correlations, so that they are transformed into the content of either the aliphatic hydrocarbon insoluble matter or asphaltene. This calculator provides for greater rapidity in the quantitative determination of these parameters.

The concept of the invention is also applicable to samples of residual fuel oils that contain both asphaltene end an insoluble matter in aliphatic hydrocarbons such as n-heptane but which do not contain any insoluble matter in aromatic hydrocarbons such as toluene.

Therefore, the invention is equally applicable whether or not the residual fuel oil sample contains the insoluble matter in aliphatic hydrocarbons such as toluene and good results are assured regardless of the presence or absence of such toluene insoluble matter.

According to the above-described method of the invention, various species of residual fuel oils could be assayed quantitatively to provide data that correlated to the values of the IP and UOP methods with 0.99 and higher coefficients of correlation. In addition, the precision of analysis which was 5% or less in terms of the coefficient of variation was better than that in analysis by the IP method in which the coefficient of variation was as high as 10%. The method requires about 40 minutes to complete one cycle of analysis but, on the other hand, it is capable of processing a number of samples at a time. Therefore, if 10 samples are to be processed, analysis takes no more than 10 minutes per sample, which is a marked decrease in the process time compared to the conventional methods of "rapid" determination.

Operation (1) Method of quantitative determination

When preparing a sample solution to be analyzed, the coagulating asphaltene particles can be allowed to have a small size and a narrow size distribution by following the procedure to be specified below and this is critical to the purpose of expanding the range over which the insoluble matter in aliphatic hydrocarbons (e.g. n-heptane) or asphaltene content can subsequently be quantitated by the dual wavelength spectrophotometric method and for improving the precision of analysis. The sample solution is stirred before, during and even after the measurement in order to ensure that the insoluble matter in aliphatic hydrocarbons (e.g. n-heptane) or asphaltene does not settle in the sample solution but can be suspended uniformly. The light from a source is guided by fiber optics to be admitted into the sample solution of a given thickness, through which the light passes. The transmitted light is picked up end the absorbance of the sample solution is measured at two different wavelengths in the range of 500 nm to 1,000 nm.

The intensities of transmitted light at the two wavelengths are converted to the values of an electric current by associated light-current transducers and subsequently fed into a computer having a predetermined program. The computer then prints out the content of the insoluble matter in aliphatic hydrocarbons (e.g. n-heptane) or asphaltene in the sample oil.

To analyze the sample solution by the dual wavelength spectrophotometric detection method, a dip probe may be submerged in the sample solution or, alternatively, the sample solution may be sucked into a flow cell. The dip probe has built-in fiber optics for admitting not only the incident light but also the two components of transmitted light and a window for introducing the sample solution and a reflector mirror are provided at the end of the dip probe. The flow cell-has fiber optics provided on one side for admitting the incident light, as well as on the other side for admitting the transmitted light. In either case, one may simply prepare a plurality of different sample solutions in order to ensure that the content of the insoluble matter in aliphatic hydrocarbons (e.g. n-heptane) or asphaltene is efficiently determined on successive different oil samples. Both the dip probe and the flow cell require that after each measurement, a cleaning solvent be passed to remove any residual sample solution that may have adhered to the probe or cell during the preceding experiment.

Whichever method is employed, all steps of the procedure for quantitative determination are controlled by the computer program to achieve considerable labor saving.

(2) Apparatus for quantitative determination (i) Dip probe system

When a container of a sample solution that is equipped with the working element of a magnetic stirrer has moved to the position of measurement where the container faces a dip probe, the magnetic stirrer is turned on to agitate the sample solution and the probe (or the container) approaches the container (or the probe) until the tip of the probe is submerged in the sample solution to the depth that is necessary and sufficient for the measurement of absorbance.

The dip probe has two built-in fiber optics bundles, one for guiding the incident light and the other for guiding the transmitted light. The light transmitted through the sample solution is guided via the associated fiber bundle, which branches in two parts and coupled to two interference filters that permit selective passage of light at different wavelengths. By passing the two components of transmitted light through the respective filters, one can determine the absorbance of the sample solution at two different wavelengths of light in the range from 500 nm to 1,000 nm.

The light passing through each filter has its intensity converted to an electric current by a light-current transducer such as a phototube or a photocell, and the resulting current values are fed into a computer having a specified program, which in turn performs the necessary mathematical operations to print out the content of the insoluble matter in aliphatic hydrocarbons (e.g. n-heptane) or asphaltene that are present in the sample oil being assayed.

When the foregoing steps complete the process of determining the content of the insoluble matter in aliphatic hydrocarbons (e.g. n-heptane) or asphaltene that are present in the oil sample, the computer sends an instruction for causing the dip probe to make a relative movement away from the sample container until the tip of the probe separates from the liquid level of the sample solution, whereupon, the computer sends another signal for opening a solenoid valve such that a cleaning solvent from a cleaner is ejected onto the probe to remove the remaining sample solution which adheres to the measuring port and other parts of the probe; the solvent that has been used in the cleaning operation is collected in the sample container. After the probe is cleaned thoroughly, the solenoid valve is closed to end the cleaning step and the sample container leaves the position of measurement (where it faces the probe) and a container of another sample solution which is furnished with the working element of a magnetic stirrer is subsequently carried to the position of measurement.

These steps complete one cycle of the process of determining the content of the insoluble matter in aliphatic hydrocarbons (e.g. n-heptane) or asphaltene that are present in the residual fuel oil sample.

(ii) Flow cell system

A system that substitutes a flow cell for the dip probe operates in essentially the same manner as described in (i). The only difference is that in the flow cell system, end faces of fiber optics bundles for guiding the incident and transmitted light are provided on the opposed sidewalls of a transparent flow cell and that the cleaner is replaced by a device for sucking in the sample solution.

The flow cell system operates in the following manner. When the end of a suction pipe connected to the flow cell is submerged in the sample solution, a vacuum pump turns on to have the sample solution introduced into the flow cell via the suction pipe. Absorbance measurements are performed on the sample solution as it flows between the opposed end faces of fiber bundle guiding the incident and transmitted light. The sucked sample solution is withdrawn into an enclosed waste liquor reservoir, which is so designed that its interior can be evacuated by discharging the air to the outside via a cold trap by a vacuum pump, so that the next sample solution is introduced into the suction pipe at a predetermined flow rate while at the same time the pump device does not be polluted by the waste liquor and gas. This sampling arrangement offers the advantage that if a cleaning solvent container is set Just behind the sample container, the suction of the cleaning solvent provides a sufficient cleaning action to remove any residual sample solution that adheres to the suction pipe, flow cell and other components; therefore, the flow cell system eliminates the need to install an independent cleaner that is necessary in the dip probe system.

The other aspects of the operation are essentially the same as described in (I).

EXAMPLES

The following examples and comparative examples are provided for the purpose of further illustrating the present invention but are by no means intended to limit the invention.

(1) Method of quantitative determination

An appropriate amount G (for example, 0.3 to 5.0 g) of a sample oil is taken into a beaker of a prescribed capacity (e.g. 100 ml). A small amount (e.g. 0.3 to 5.0 ml, preferably 1.0 ml) of toluene is added so that the asphaltene is dissolved whereas large toluene-insoluble particles are suspended. Then, a prescribed amount (e.g. 100 ml) of heated (about 80° C.) n-heptane is added and the mixture is stirred to coagulate the asphaltene. Thereafter, the mixture is left to cool at room temperature for about 30 minutes to prepare a sample solution.

For improving the stability of the particles of the asphaltene and the toluene-insoluble matter, surfactants, dispersants for engine oils, etc. may be added such as to control the tendency of those particles to sediment.

The above-described sequence of the process for preparing the sample solution generates asphaltene particles of a narrow size distribution between 1 to 3 μm and is critical to the purpose of expanding the range over which the content of asphaltene can be determined by the subsequent dual wavelength spectrophotometric detection method and for improving the precision of analysis.

The sample solution thus prepared is agitated with a magnetic stirrer or by other suitable means and the absorbance of the sample solution is measured at 800 nm and 750 nm without removing the dissolved asphaltene and the suspended toluene-insoluble matter.

Referring to FIG. 1, let us suppose that the absorbance of the sample solution is measured as $K_3=1.10$(at 800 nm) and $K_4=1.38$(at 750 nm). Based on the relationship between $K_4/K_3$ and the content of the n-heptane insoluble matter, the system employed in the example under consideration gives the following relations Concentration (mass%) of n-heptane insoluble matter $(2A.HI)= 0.025 \times (7K_3-5K_4) \times 100/G$.

The coefficient of variation is calculated by the following equation for 6 measurements:

Coefficient of variation (%)=

(S. D. expressed in terms of the square root of unbiased variance)×100/mean value of six measurement)

To determine the fraction of the 2A.HI value divided by the UOP.HI value (i.e., the relative proportion of n-heptane insoluble matter), the rate of increase in the absorbance of the sample solution as calculated by $(K_4-K_3) \times 100/K_3$ is inserted into the following equation:

Relative proportion of n-heptane insoluble matter=−5.996 (rate of increase in the absorbance of sample solution)+216     (14)

The thus determined relative proportion of the n-heptane insoluble matter is inserted into the following equation to calculate the weight of the n-heptane insoluble matters:

Content of n-heptane insoluble matter=2A.HI×100 /relative proportion of n-heptane insoluble matter     (15)

Combining Eqs. 14 and 15, one can obtain the following equations:

Content of n-heptane insoluble matter=$\{0.025(7K_3-5K_4)\} \times 100$ /$\{-5.996(K_4-K_3) \times 100/K_3+216\}$     (16)

Thus, the content of the n-heptane insoluble matter can be determined on the basis of the values of $K_3$ and $K_4$ measured on the sample solution at two wavelengths and it is divided by the weight of the residual fuel oil sample to yield the content of the n-heptane insoluble matter.

The corrected 2A-HI value correlated well with the UOP.HI value and the coefficient of correlation was 0.992. The corrected relative proportion of 2A.HI was within 100 ±15%.

The next step is for determining the content of asphaltene. To this end, the fraction of the IP.AS value that is divided by the UOP.HI value (i.e., IP.AS fraction) is determined from the rate of increase in the absorbance of the sample solution by the following equations:

IP.AS fraction=5.59 (rate of increase in the absorbance of sample solution)−1.93     (17)

To determine the weight of the asphaltene content, the content of n-heptane insoluble matter ns calculated by Eq. 15 or 16 and the IP.AS fraction as calculated by Eq. 17 are inserted into the following equation:

Asphaltene content=content of n-heptane insoluble matter×IP.AS fraction/100     (118)

The thus determined weight of the asphaltene content is divided by the weight of the residual fuel oil sample to give the content of the asphaltene content.

The content of asphaltene thus determined correlated well with the IP.AS content and the coefficient of correlation was 0.997. The results of measurements on actual samples are set forth in Table 1 below. It should be added that essentially the same results were attained by the flow cell system.

TABLE 1

| sample | Asphaltene (mass %) | | | n-Heptane insolubles (mass %) | | |
|---|---|---|---|---|---|---|
| | IP method | 2A method | Inventive method | UOP method | 2A method | Inventive method |
| Without toluene-insolubles | | | | | | |
| 1 | 0.57 | 0.57 | 0.57 | 0.57 | 0.57 | 0.57 |
| 2 | 4.63 | 4.79 | 4.76 | 4.55 | 4.79 | 4.76 |
| With toluene-insolubles | | | | | | |
| 3 | 0.45 | — | 0.52 | 0.95 | 1.63 | 1.02 |
| 4 | 1.09 | — | 0.98 | 1.62 | 2.71 | 1.67 |

(2) Apparatus for quantitative determination
  (i) Dip probe system

Figure 2:
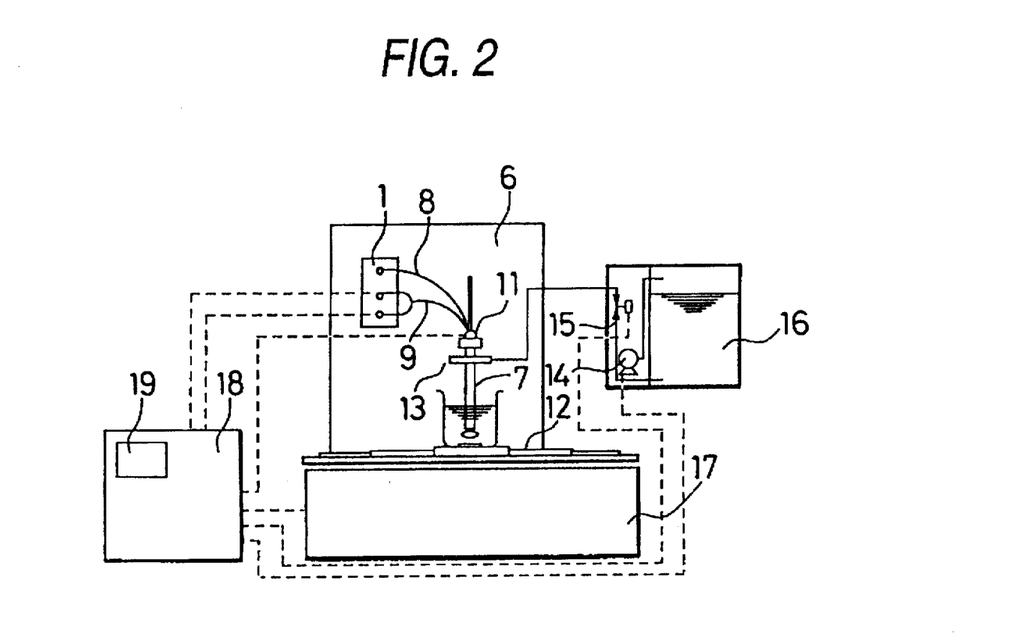
FIG. 2 shows schematically an apparatus for automatic quantitative determination on a residual fuel oil using a dip probe system according to an embodiment of the invention.
Figure 3:
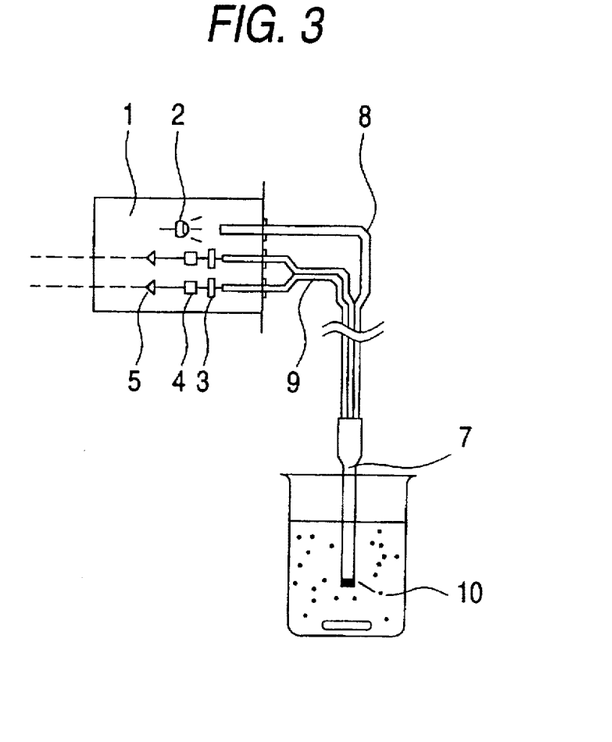
FIG. 3 is an enlarged view of the two-wavelength absorbance detector in FIG. 2.

FIG. 2 shows schematically an apparatus for determining the content of asphaltene by the dip probe system, and FIG. 3 shows enlarged the essential part of the apparatus. As shown, a two-wavelength absorbance detector 1 includes two major parts: a photometric portion that includes a light source 2 (e.g. tungsten lamp), interference filters 3 (one operating at 750 nm and the other at 800 nm), phototubes (or solar cells) 4 and amplifiers 5, and a dip probe 7 enclosed in an elevator 6. The two major parts are coupled together by a fiber optics bundle 8 for guiding the incident light and another optics bundle 9 for guiding the transmitted light. As shown clearly in FIG. 3, the dip probe 7 has an opening (e.g. h =3 mm and w =8 mm) and a reflector mirror 10 at the bottom end; the probe is held by a holder 11 in the elevator 6 (see FIG. 2) such that it descends to be submerged in the sample solution in the measurement mode whereas it is lifted above the sample solution in the cleaning step and while a turntable 12 rotates.

Referring to FIG. 2, the elevator 6 is equipped with a plurality of probe cleaning nozzles 13 that are arranged in an annular pattern to surround the dip probe; these nozzles are connected via a Teflon tube to a cleaning solvent tank 16 equipped with a miniature compressor 14 and a solenoid valve 15. Elevator 6 is fixed to an automatic sample feeder 17 having the turntable 12 (which may receive 12 beakers) and a magnetic stirrer that is located in the position of measurement. Elevator 6, miniature compressor 14 and turntable 12 are turned on or off end solenoid valve 15 is opened or closed under the control of instructions issued from microcomputer 18. The output current from the two-wavelength absorbance detector 1 is fed into microcomputer 18, where the current is converted to the contents of n-heptane insoluble matter and asphaltene which, in turn, are delivered from a printer 19 in the form of a printout.

Stated more specifically, in response to a signal issued form the microcomputer 18, the magnetic stirrer on the automatic sample feeder 17 starts to rotate, whereupon the sample solution in e beaker that is set in the position of measurement is agitated. At the same time, elevator 6 turns on to descend the probe holder 11 until the opening of the dip probe 7 is submerged in the sample solution. Incident light issuing from the source 2 in the detector 1 passes through the fiber bundle 8 to reach the dip probe, from which it is admitted into the sample solution through the open end. The admitted incident light is partly absorbed by the sample solution and partly reflected by mirror 10. The reflected light is partly absorbed in the return path and the remainder is transmitted through the sample solution such that it is guided via the fiber bundle 9 to reach interference filters 3, which allow selective passage of the transmitted light at two specified wavelengths. The intensities of the transmitted light at the two wavelengths are then fed into respective phototubes 4, where they are converted to the values of an electric current which, in turn, are amplified by amplifiers 5 before they are fed into the microcomputer 18.

In the microcomputer 18, the input current is converted to transmittance T ($=I/I_0$, where I is the intensity of transmitted light and $I_0$ is the intensity of incident light) which, in turn, is converted to absorbance K ($=\log_{10} 1/T$). By applying a preliminarily loaded correlation between the rate of increase in the absorbance of the sample solution and the blank rate and also based on a preloaded calibration curve plotting $K_3-K_4$ against the content of n-heptane insoluble matter, microcomputer 18 calculates the contents of n-heptane insoluble matter and asphaltene from the obtained date on absorbance K and delivers those contents into printer 19. Microcomputer 18 is also preliminarily loaded with the correlation between the inventive method and the IP method and that between the inventive method and the UOP method; hence, using these correlations, microcomputer 18 converts the calculated contents of n-heptane insoluble matter and asphaltene to the IP content of asphaltene and the UOP content of n-heptane insoluble matter, respectively, which are delivered to the printer 19 for printout. Upon completion of the necessary inputs, microcomputer 18 issues signals, in response to which the miniature compressor 14 is turned on and the interior of cleaning solvent tank 16 is pressurized; subsequently, elevator 6 is turned on such that probe holder 11 starts to ascend and, at the same time, the solenoid valve 15 opens and the cleaning solvent (e.g. n-heptane) is ejected from nozzles 13 to clean the dip probe 7.

Subsequently, automatic sample feeder 17 turns on and the turntable 12 rotates such that the next sample solution to be assayed is set in the position of measurement and the operations described above are repeated automatically.

If the sample to be measured is such that the dip probe 7 can be cleaned only with difficulty by ejecting the cleaning solvent through the nozzles, better cleaning effects can be achieved by setting up beakers on the turntable 12 in such a way that a beaker containing the sample solution alternates with a beaker containing the cleaning solvent (e.g. toluene).

(ii) Flow cell system

Figure 4:
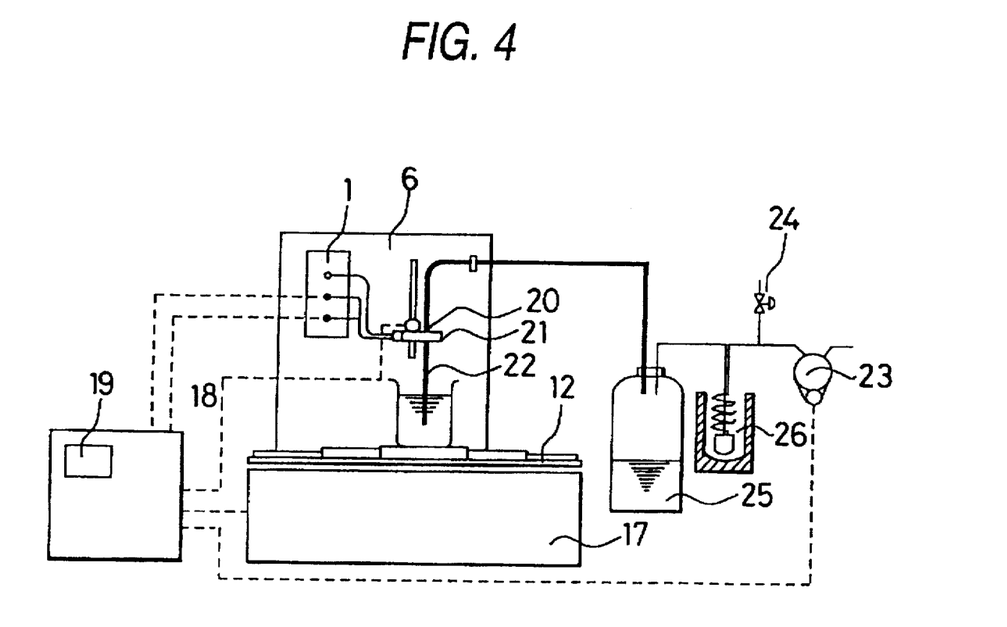
FIG. 4 shows schematically an apparatus for automatic quantitative determination on a residual fuel oil using a flow cell system according to another embodiment of the invention.

FIG. 4 shows schematically an apparatus for determining the content of asphaltene by the flow cell system. In response to signals issued from a microcomputer 18, elevator 6 turns on and a flow cell 20 (for example, made of glass in a thickness of 3 mm) fixed to a holder 21 in the drive unit of the elevator starts to descend until the end of a suction pipe 22 (for example, a Teflon tube having an inside diameter of 2 mm) which is coupled to the bottom end of the flow cell 20 is submerged in the sample solution in a beaker on the turntable 12 in the position of measurement as the sample solution is being agitated with a magnetic stirrer installed on an automatic sample feeder 17.

Subsequently, a vacuum pump 23 turns on to cause the sample solution to be drawn into the flow cell 20 at a flow rate (desirable 10 to 30 mL/min) that is created by the suction pressure that has been adjusted by a pressure control valve 24. When the sample solution passes through the flow cell 20, the two-wavelength absorbance detector 1 senses the transmitted light through the sample solution at two wavelengths (e.g. 750 nm and 800 nm) and converts the intensities of the two components of the transmitted light to the values of an electric current, which are fed into the microcomputer 18 and converted to absorbance data for storage in the computer. Entry of electric current values into the microcomputer 18 is preferably performed about 20 seconds after the vacuum pump 23 turned on.

When one cycle of measurement is complete, the drive unit of elevator 6 ascends to lift the suction pipe 22 above the sample solution. In a few seconds the vacuum pump 23 turns off. The vacuum pump is preferably driven for a period of about 60 seconds. In the next step, the automatic sample feeder 17 turns on and the turntable 12 rotates such that a beaker containing the cleaning solvent (toluene) is set in the position of measurement. The vacuum pump 23 turns on again and the solvent is sucked in to clean the inner surfaces of the suction pipe 22 and the flow cell 20. After the end of the cleaning step, the turntable 12 rotates again and the next sample solution to be analyzed is set in position for another cycle of measurement.

The sequence of the above-described operations is controlled by the programmed microcomputer 18. After the end of measurement on one sample, the results of quantitative determination of the n-heptane insoluble matter and asphaltene are successively delivered from the printer 19 in response to a printout instruction sent to the microcomputer 18.

The sample solution and cleaning solvent that have been drawn are collected in a waste liquor reservoir 25. In order to ensure against pollution of the vacuum pump 23, a cold trap 26 is desirably inserted downstream of the reservoir 25.

In FIG. 4, the holder 21 to which the flow cell 20 is fixed and the two-wavelength absorbance detector 1 are coupled to elevator 6. It should however be noted that the flow cell 20 and the holder 21 for fixing it may be provided in any position of the pipeline for the passage of the sample solution that has been drawn in through the suction pipe 22 and it is not absolutely necessary to fix them on the elevator 6. This is also the case with the two-wavelength absorbance detector 1 and it need not necessarily be fixed on the elevator 6. However, the end of the suction pipe 22 need be vertically movable such that it can be submerged into or lifted above the sample solution as required; therefore, if the flow cell holder 21 is not fixed on the elevator 6, the suction pipe 22 may be fixed to the elevator 6 at a site near the end of the pipe 22.

The method and apparatus of the invention offer the advantage that even if the sample oil to be analyzed is a residual fuel oil containing the particles of an insoluble matter in aromatic hydrocarbons such as toluene, the contents of an insoluble matter in aliphatic hydrocarbons (e.g. n-heptane) and asphaltene can be determined in a precise and rapid manner. The invention is also applicable to residual fuel oils that do not contain any matter that is insoluble in aromatic hydrocarbons such as toluene. Therefore, the invention is very useful in practical applications.

What is claimed is:

1. A method of determining a content of an aliphatic hydrocarbon insoluble matter in a residual fuel oil, the method comprising the steps of:

(a) measuring absorbances of a sample solution having an aliphatic hydrocarbon insoluble matter suspended in the sample solution at two spaced wavelengths of light in a wavelength range from 500 nm to 1,000 nm; and (b) performing an operation to determine the content of the aliphatic hydrocarbon insoluble matter in the sample solution by inserting the measured absorbances ($K_3$ and $K_4$) into one of two correlations:

$$\text{the content of the aliphatic hydrocarbon insoluble matter} = \{a(bK_3 - cK_4)\} \times 100 / \{d((K_4 - K_3) \times 100/K_3) + e\}$$

where a is 0.015 to 0.035; b is 1 to 10; c is 0.5 to 7; d is −10 to −0.1; and e is 50 to 300; or $$\text{the content of the aliphatic hydrocarbon insoluble matter} = \{a(bK_3 - cK_4)\} \times 100 / \{d(K_4 \times 100/K_3) + e\}$$

where a is 0.015 to 0.035; b is 1 to 10; c is 0.5 to 7; d is −800 to −500; and e is 500 to 1,000.

2. The method of claim 1, wherein the sample solution is prepared by adding an aromatic hydrocarbon to a sample of the residual fuel oil to dissolve in each other, and then adding an aliphatic hydrocarbon to the dissolved solution to coagulate the aliphatic hydrocarbon insoluble matter.

3. The method of claim 2, wherein the aliphatic hydrocarbon is added to the dissolved solution after being heated at a temperature of 40° to 90° C., and the sample solution is cooled at a temperature of 25° to 30° C. before the step (a).

4. The method of claim 1, wherein the two spaced wavelengths are at least 10 nm away from each other.

5. A method of determining a content of asphaltene in a residual fuel oil, the method comprising the steps of:

(a) measuring absorbances of a sample solution having an aliphatic hydrocarbon insoluble matter suspended in the sample solution at two spaced wavelengths of light in a wavelength range from 500 nm to 1,000 nm; and (b) performing an operation to determine the content of the asphaltene in the sample solution by inserting the measured absorbances ($K_3$ and $K_4$) into one of two correlations:

$$\text{the content of asphaltene} = \{a(bK_3 - cK_4)\}' 100 / \{d((K_4 - K_3) \times 100/K_3) + e\} \times \{f((K_4 - K_3) \times 100/K_3) + g\}/100$$

where a is 0.015 to 0.035; b is 1 to 10; c is 0.5 to 7; d is −10 to −0.1; e is 50 to 300; f is 1 to 30; and g is −5 to 5; or $$\text{the content of asphaltene} = \{a(bK_3 - cK_4)\} \times 100 / \{d(K_4 \times 100/K_3) + e\} \times \{f(K_4 \times 100/K_3) + g\}/100$$

where a is 0.015 to 0.035; b is 1 to 10; c is 0.5 to 7; d is −800 to −500; e is 500 to 1,000; f is 450 to 550; and g is −600 to −300.

6. The method of claim 5, wherein the sample solution is prepared by adding an aromatic hydrocarbon to a sample of the residual fuel oil to dissolve in each other, and then adding an aliphatic hydrocarbon to the dissolved solution to coagulate the aliphatic hydrocarbon insoluble matter.

7. The method of claim 6, wherein the aliphatic hydrocarbon is added to the dissolved solution after being heated at a temperature of 40° to 90° C., and the sample solution is cooled at a temperature of 25° to 30° C. before the step (a).

8. The method of claim 5, wherein the two spaced wavelengths are at least 10 nm away from each other.

9. An apparatus for determining a content of an aliphatic hydrocarbon insoluble matter in a residual fuel oil, the apparatus comprising:

a container for containing a sample solution which has an aliphatic hydrocarbon insoluble matter suspended in the sample solution;

a measuring device for measuring absorbances of the sample solution by transmitting light at two spaced wavelengths in a wavelength range from 500 to 1,000 nm to the sample solution and for outputting electric signal in accordance with the measured absorbances; and a calculator for calculating the content of the aliphatic hydrocarbon insoluble matter from the electric signals, the calculator performing an operation with one of two correlations:

the content of the aliphatic hydrocarbon insoluble matter=$\{a(bK_3-cK_4)\}\times 100/\{d((K_4-K_3)\times 100/K_3)+e\}$ where a is 0.015 to 0.035; b is 1 to 10; c is 0.5 to 7; d is −10 to −0.1; e is 50 to 300; and $K_3$ and $K_4$ are the absorbances at the two spaced wavelengths; or the content of the aliphatic hydrocarbon insoluble matter=$\{a(bK_3-cK_4)\}\times 100/\{d(K_4\times 100/K_3)+e\}$ where a is 0.015 to 0.035; b is 1 to 10; c is 0.5 to 7; d is −800 to −500; e is 500 to 1,000; and $K_3$ and $K_4$ are the absorbances at the two spaced wavelengths.

10. The apparatus of claim 9, wherein the measuring device comprises a dip probe for dipping into the sample solution in the container.

11. The apparatus of claim 9, wherein the measuring device comprises a flow cell having a suction pipe which is coupled to the container and a suction device for drawing the sample solution into the flow cell through the suction pipe.

12. The apparatus of claim 9, wherein the measuring device comprises a light source, a light passage for leading the light from the light source to the container, interference filters for transmitting the light only at the two spaced wavelengths, and convertors for converting intensities of the transmitted light to the electric signal.

13. The apparatus of claim 9, further comprising: a sample feeder for preparing the sample solution by adding an aromatic hydrocarbon to a sample of the residual fuel oil to dissolve in each other and then adding the aliphatic hydrocarbon to the dissolved solution to coagulate the aliphatic hydrocarbon insoluble matter; and a cleaning device for removing the sample solution from the measuring device.

14. The apparatus of claim 13, wherein the sample feeder comprises means for adding the aliphatic hydrocarbon to the dissolved solution after being heated at a temperature of 40° to 90° C. and means for cooling the sample solution at a temperature of 25° to 30° C. before measuring the absorbances.

15. An apparatus for determining a content of asphaltene in a residual fuel oil, the apparatus comprising:

a container for containing a sample solution which has an aliphatic hydrocarbon insoluble matter suspended in the sample solution;

a measuring device for measuring absorbances of sample solution by transmitting light at two spaced wavelengths in a wavelength range from 500 to 1,000 nm to the sample solution and for outputting electric signal in accordance with the measured absorbances; and a calculator for calculating the content of the asphaltene from the electric signal, the calculator performing an operation with one of two correlations:

the content of asphaltene=$\{a(bK_3-cK_4)\}\times 100/\{d((K_4-K_3)\times 100/K_3)+e\}\times\{f((K_4-K_3)\times 100/K_3)+g\}/100$ where a is 0.015 to 0.035; b is 1 to 10; c is 0.5 to 7; d is −10 to −0.1; e is 50 to 300; f is 1 to 30; g is −5 to 5; and $K_3$ and $K_4$ are the absorbances at the two selected wavelengths; or the content of asphaltene=$\{a(bK_3-cK_4)\}\times 100/\{d(K_4\times 100/K_3)+e\}\times\{f(K_4\times 100/K_3)+g\}/100$ where a is 0.015 to 0.035; b is 1 to 10; c is 0.5 to 7; d is −800 to −500; e is 500 to 1,000; f is 450 to 550; g is −600 to −300; and $K_3$ and $K_4$ are the absorbances at the two selected wavelengths.

16. The apparatus of claim 15, wherein the measuring device comprises a dip probe for dipping into the sample solution in the container.

17. The apparatus of claim 15, wherein the measuring device comprises a flow cell having a suction pipe which is coupled to the container and a suction device for drawing the sample solution into the flow cell through the suction pipe.

18. The apparatus of claim 15, wherein the measuring device comprises a light source, a light passage for leading the light from the light source to the container, interference filters for transmitting the light only at the two spaced wavelengths, and convertors for converting intensities of the transmitted light to the electric signals.

19. The apparatus of claim 15, further comprising:

a sample feeder for preparing the sample solution by adding an aromatic hydrocarbon to a sample of the residual fuel oil to dissolve in each other and then adding the aliphatic hydrocarbon to the dissolved solution to coagulate the aliphatic hydrocarbon insoluble matter; and a cleaning device for removing the sample solution from the measuring device.

20. The apparatus of claim 19, wherein the sample feeder comprises means for adding the aliphatic hydrocarbon to the dissolved solution after being heated at a temperature of 40° to 90° C. and means for cooling the sample solution at a temperature of 25° to 30° C. before measuring the absorbances.

* * * * *